United States Patent [19]

Klingenbeck-Regn

[11] Patent Number: 5,787,887
[45] Date of Patent: Aug. 4, 1998

[54] APPARATUS FOR TISSUE EXAMINATION USING BIDIRECTIONAL TRANSIRRADIATION WITH LIGHT

[75] Inventor: Klaus Klingenbeck-Regn, Nürnberg, Germany

[73] Assignee: Siemens Aktiengesellschaft, Munich, Germany

[21] Appl. No.: 648,179

[22] PCT Filed: Nov. 11, 1994

[86] PCT No.: PCT/DE94/01332

§ 371 Date: May 21, 1996

§ 102(e) Date: May 21, 1996

[87] PCT Pub. No.: WO95/14427

PCT Pub. Date: Jun. 1, 1995

[30]   Foreign Application Priority Data

Nov. 24, 1993 [DE] Germany .................. 43 40 072.8

[51] Int. Cl.$^6$ ...................................................... A61B 5/00

[52] U.S. Cl. .................. 128/653.1; 128/633; 128/664; 128/665; 356/398

[58] Field of Search ............................ 128/664, 665, 128/633; 356/39, 40, 41, 398; 250/339.01, 345, 349, 341.7

[56]  References Cited

U.S. PATENT DOCUMENTS 5,309,907  5/1994  Fang et al. ............................. 128/633

Primary Examiner—Marvin M. Lateef
Assistant Examiner—Eleni Mantis Mercader

[57]   ABSTRACT

An apparatus for examining tissue with light, for identifying inhomogeneities, such as tumors, in the tissue, bidirectionally transirradiates the tissue with light, and detects the light emerging from the tissue in the two directions, thereby providing different images of the tissue with the inhomogeneities therein represented with different contrast, thereby making identification of the inhomogeneity easier.

19 Claims, 6 Drawing Sheets 5,787,887

APPARATUS FOR TISSUE EXAMINATION USING BIDIRECTIONAL TRANSIRRADIATION WITH LIGHT

BACKGROUND OF THE INVENTION

1. Field of the Invention

The invention is directed to an apparatus for examining tissue with light.

2. Description of the Prior Art

Known apparatuses for examining tissue with light can operate with visible, NIR or IR light. The wavelength of the visible light lies between 380 and 780 nm, that of NIR light, i.e. of near-infrared light, lies between 780 nm and 1.5 μm and that of IR light, i.e. of infrared light, lies between 1.5 μm and 1 mm, whereby the wavelength range from 660 nm through 1.2 μm is especially suitable.

Many optical properties of tissue, for example the absorption, the scatter and the spectral properties, can be identified by irradiation with light. For example, it is therefore possible in mammary diagnostics to identify tissue modifications in that light is beamed into the mammary, the light emerging therefrom is detected and the information acquired in this way is interpreted in a suitable way.

The problem arises in known apparatus (see, for example, German OS 41 28 744) that the information acquired by detecting the emerging light can only be interpreted with difficulty since the contrast between potential inhomogeneities and the surrounding tissue is often too low.

SUMMARY OF THE INVENTION

The invention is therefore based on the object of fashioning an apparatus of the type initially described wherein the information acquired by detecting the emerging light can be interpreted better.

This object is inventively achieved in an apparatus for examining tissue with light comprising a) means for the bidirectional transirradiation of the tissue under examination with light, and b) means for detection that are provided for the purpose of detecting parts of the light emanating from the means for detection transmitted through the tissue under examination for both transirradiation directions.

As used herein, bidirectional transirradiation means that work is carried out with two opposite transirradiation directions, whereby the optical axis is substantially the same for both transirradiation directions. As a result of the great scatter to which light is subjected to in the tissue in the transirradiation of tissue, inhomogeneities or absorbers contrast more highly from the surrounding tissue the closer they lie to the means for detection, i.e. to that surface through which the light to be detected emerges from the tissue. Since transirradiation is bidirectional given the inventive apparatus, a different contrast with which the inhomogeneity contrasts with the surrounding material is achieved for the two transirradiation directions, except for that special case wherein an inhomogeneity has the same spacing from the means for detection for both transirradiation directions. Information that can be interpreted better is thus available since the more beneficial, i.e. higher-contrast information can be used to form the basis for the interpretation. At the same time, information is acquired as to whether an inhomogeneity lies closer to the one or to the other surface that limits the transirradiated tissue region in transirradiation direction.

In order to prevent the properties of the transirradiated tissue from being able to change significantly during the time that elapses between the transirradiation in the two transirradiation directions, in a version of the invention provides that the bidirectional transirradiation ensues quasi-simultaneously. In a further version of the invention the means for transirradiating the tissue under examination in fact transirradiate simultaneously in both transirradiation directions. A mutual influencing of the two transirradiation directions can be avoided by differently modulating the light respectively in the two transirradiation directions. The light for the two transirradiation directions is preferably amplitude-modulated with different modulation frequencies. As a result of the different modulation, it is easily possible to use only the light for the two transirradiation directions by demodulating the output signal of the means for detection in a suitable way.

In order to prevent mutual influencing of the two transirradiation directions, diaphragm means can also be provided that keep the light emanating from the means for transirradiation away from the means for detection in alternation for the one or the other transirradiation direction.

According to another version of the invention, the means for transirradiation have first and second light sources and the means for detection have first and second detector devices, whereby the light emanates from the first light source in the one transirradiation direction, and the first detector device is provided for detecting parts of the light emanating from the first light source that are transmitted through the tissue, and whereby the light in the other transirradiation direction emanates from the second light source and the second detector device is provided for detecting parts of the light emanating from the second light source that are transmitted through the tissue. According to an embodiment of the invention, the first light source and the first detector means can be active simultaneously with the second light source and the second detector means simultaneously active. Alternatively the first light source and the first detector means can be operated in alternation with the second light source and the second detector means.

In a further version of the invention the means for transirradiation comprise a light source to which lightguide means that transmit the light of the light source in the one or in the other transirradiation direction in alternation are allocated. The technological outlay can be reduced in this way. This is also true when the means for detection comprise a detector device to which lightguide means are allocated for the purpose of conducting light to be detected to the detector device in alternation with respect to the one or the other transirradiation direction.

The lightguide means can, for example, contain beam splitters and mirrors. According to another embodiment of the invention, which is preferred because of its technological simplicity, the lightguide means contain fiber-optic means, for example optical fibers. The fiber-optic means can also contain a bundle of optical fibers that contains at least one optical fiber conducting light in a transirradiation direction emanating from the means for transirradiation to the tissue under examination, and at least one optical fiber conducting a transmitted part of the light in the other transirradiation direction to the means for detection. An especially high degree of coincidence of the optical axes for the two transirradiation direction is achieved particularly when such optical fiber bundles are employed at both sides of the tissue under examination.

In order to also be able to examine larger tissue regions, in a preferred embodiment of the invention scan means are provided with which the bidirectional transirradiation of the tissue under examination ensues in a plurality of scan positions. There is thus the possibility of producing, so to speak, images of the tissue region under examination in the transmission procedure. This occurs with the assistance of evaluation means to which the output signals of the means for detection are supplied. When an offset of the two transirradiation directions is present as a consequence of deviating optical axes, according to a modification of the invention the evaluation means eliminate the offset. This can occur with methods that are standard in image processing. An offset can be especially easily eliminated when the offset is equal in terms of amount and direction to the offset between two neighboring scan positions or a whole multiple thereof. The offset between the images produced for the two transirradiation directions can then be eliminated in that picture elements respectively belonging to allocated scan positions are allocated to one another.

In order also to be able to implement spectroscopic examinations, in a modification of the invention that the means for transirradiation simultaneously emit having defined, different wavelengths, and the means for detection emit a plurality of signals corresponding in number to the plurality of different wavelengths, the signals respectively corresponding to that part of the light of one of the different wavelengths in the detected part of the light transmitted through the tissue that emanates from the means for transirradiation.

DESCRIPTION OF THE PREFERRED EMBODIMENTS

Figure 1:
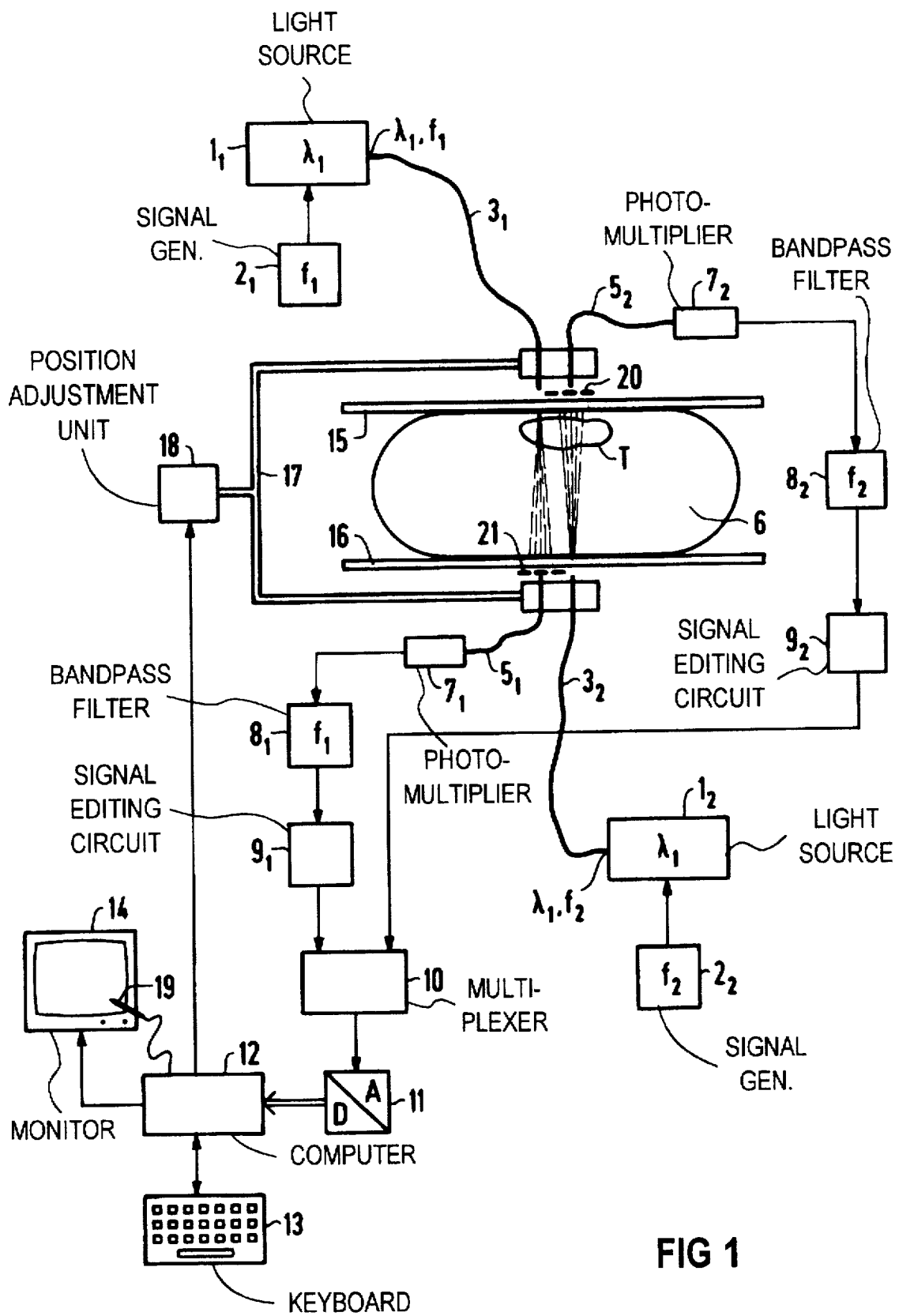
FIGS. 1, 2, 3 and 4 are respective circuit diagrams of first second, third and fourth embodiments of an apparatus for examining tissue with light constructed in accordance with the principles of the present invention.

FIG. 1 shows an inventive apparatus that, for example, can be employed for mammary diagnostics. The apparatus has two light sources $1_1$ and $1_2$, each of which emits coherent light with the wavelength $\lambda_1$. Each of the light sources $1_1$ and $1_2$ contains a semiconductor laser diode and an associated power supply. The light sources $1_1$ and $1_2$ have a respective electrical signal generators $2_1$ and $2_2$ allocated to them that supply an alternating current signal having a fixed frequency with which the supply current of the semiconductor laser diode contained in the respective light sources $1_1$ and $1_2$ is modulated. Each of the signal generators $2_1$ and $2_2$ generates an alternating current signal having a different frequency $f_1$ or $f_2$. Since the amplitude or intensity of the light emitted by the laser diodes is essentially proportional to the intensity of the current of their supply current, the light sources $1_1$ and $1_2$ thus emit light of the wavelength $\lambda_1$ that is amplitude-modulated with respectively different modulation frequency $f_1$ or $f_2$.

The light emitted by the light sources $1_1$ and $1_2$ is supplied via respective fiber-optic light waveguides $3_1$ and $3_2$ to the tissue under examination, i.e. the subject 6, for example a mammary. The subject 6 is arranged between two planar compression plates 15 and 16 that are arranged parallel to one another and that are essentially transparent for the light of the light sources $1_1$ and $1_2$.

The ends of the light waveguides $3_1$ and $3_2$, which form the light exit zones of the apparatus, are arranged at different sides of the subject 6 lying approximately opposite one another, such that, leaving the optical scatter in the tissue of the subject 6 out of consideration, the tissue regions traversed—in opposite direction—by the light of the two light sources $1_1$ and $1_2$ do not significantly differ from one another, differing from the non-overlapping representation shown in FIG. 1 for reasons of clarity. A tissue region of the subject 6 under examination can thus be bidirectionally transirradiated with light arising from the light sources $1_1$ and $1_2$.

Two photomultipliers $7_1$ and $7_2$ to which the parts of the transmitted light emerging from the subject 6 are supplied via respective fiber-optic light waveguides $5_1$ and $5_2$ are provided for detecting the parts of the light transmitted through the subject 6. Just like the free ends of the light guides $3_1$ and $3_2$, the free ends of the light waveguides $5_1$ and $5_2$ that form the light entry zones of the apparatus are arranged as close as possible to the subject 6 under examination, i.e. at the corresponding compression plate 15 or 16.

It is self-evident that the part of the light transmitted through the subject 6 that arises from the light source $1_1$ is to be detected with the photomultiplier $7_1$, and the part of the light transmitted through the subject in the opposite direction that arises from the light source $1_2$ is to be detected with the photomultiplier $7_2$. The output signals of the photomultipliers $7_1$ and $7_2$ are supplied to respective band-pass filters $8_1$ and $8_2$. The center frequencies of the band-pass filters $8_1$ and $8_2$ are selected such that they respectively coincide as exactly as possible with the frequencies $f_1$ and $f_2$ with which the respective light of the light sources $1_1$ and $1_2$ is amplitude-modulated. Signals that exclusively represent the parts of the light of the light source $1_1$ or of the light source $1_2$ transmitted through the subject 6 are thus respectively available at the output of the band-pass filters $8_1$ and $8_2$. Those parts of the output signals of the photomultipliers $7_1$ and $7_2$ that represent the ambient light and light arising from the light sources $1_2$ and $1_1$ cannot pass the band-pass filters $8_1$ or $8_2$.

The band-pass filters $8_1$ and $8_2$ are followed by signal processing means in the form of respective signal editing circuits $9_1$ and $9_2$ that effect a signal editing adapted to the particular examination case, for example by rectification, smoothing or integration. The output signals of the signal editing circuits $9_1$ and $9_2$ are supplied to a 2:1 analog multiplexer 10 whose output is connected to the input of an analog/digital converter 11. The digital output data of the analog/digital converter 11 proceed to an electronic computational unit 12 that, among other things, serves the purpose of controlling the apparatus and to which a keyboard 13 serving for the operation of the measuring apparatus and a monitor 14 are connected.

In order to be able to collect data with respect to larger regions of the subject 6, the light waveguides $3_1$ and $5_2$ on the one hand and $3_2$ and $5_1$ on the other hand are attached to a carrier 17 that can be adjusted with an adjustment unit 18 controlled by the electronic computational means 12 such that the light exit and light entry zones of the measuring apparatus can be adjusted in common relative to the subject 6 in the fashion of a scan motion. For example, data for 100 positions of the carrier 17 can be collected during the course of the scan motion, these positions being arranged matrix-like in ten rows and columns and having the same spacing from one another in both row and column directions. The data obtained in the preferably serpentinve-like scan motion are preferably graphically displayed on the monitor 14 by the electronic computational means 12, whereby different intensities of the detected light are indicated by different gray-scale or chromatic values.

Since, given the transirradiation of tissue with light, an inhomogeneity is displayed with increasingly higher contrasts the closer it is located to that limiting surface of the subject to which the detector or the light entry zone is allocated, and since the subject 6 is bidirectionally transirradiated given the inventive apparatus, two high-contrast "images" are produced during the scanning of the subject 6, in which an inhomogeneity, for example at tumor T, is portrayed with different degrees of high-contrast. One image is allocated to one transirradiation direction and the other is allocated to the other transirradiation direction. The electronic computational unit 12 stores the data belonging to the two images in such a way that it is always able to tell which data belong to which of the two images.

In a first operating mode of the apparatus, the electronic computational unit 12 simultaneously displays two images that respectively correspond to the two transirradiation directions on the monitor 14. Using a light pen 19, an operator can select only that image in which the particular inhomogeneity of interest is displayed with greater contrast. The corresponding image is then displayed by itself on the monitor 14 in enlarged format.

In a second operating mode, there is the possibility of marking one or more areas in one of the two images with the light pen 19, whereupon the electronic computational unit 12 blanks out the corresponding areas on the other image and mixes the marked areas in instead. This operating mode is particularly advantageous when a plurality of inhomogeneities are present, some of which are displayed with higher contrast in the one image and other of which are displayed with higher contrast in the other image, since one or more inhomogeneities displayed with less contrast in one image can then be replaced by corresponding excerpts from the other image.

In another operating mode of the apparatus, the electronic computational unit 12 evaluates the images respectively corresponding to the two different transirradiation directions with known methods of image processing and forms a single image with maximum contrast from the data of the two images, this being displayed on the monitor 14.

It is clear from the above comments that the bidirectional transirradiation of the subject 6 ensues simultaneously, which is advantageous since the data corresponding to the two transirradiation directions for the individual scan positions are identified simultaneously, and thus under identical conditions. Under certain circumstances, however, light of the light source $1_1$ or of the light source $1_2$, reflected at the surface of the subject can lead to overexposures of the photomultiplier $7_2$ or $7_1$ resulting in measuring errors and possibly damaging one or both of the photomultipliers $7_1$ and $7_2$. In order to alleviate this situation, the electronic computational unit 12 can activate the light sources $1_1$ and $1_2$ in alternation. Alternatively, diaphragm units 20 and 21 (schematically shown in FIG. 1, which can be constructed similar to a camera shutter can be attached to the carrier 17 and can be actuated in alternation such that the light of the light source $1_1$ is kept away from the photomultiplier $7_2$ or the light of the light source $1_2$ is kept away from the photomultiplier $7_1$. The alternating actuation of the diaphragm units 20 or also ensues 21 with the electronic computational unit 12. In the case of FIG. 1, the diaphragm units 20 and 21 are respectively arranged between the subject 6 and the free ends of the optical fibers $5_1$ and $5_2$. Of course, there is also the possibility of arranging the diaphragm units 20 and 21 respectively between the subject 6 and the free ends of the optical fibers $3_2$ and $3_1$. There is also the possibility of allocating one diaphragm unit to the free end of one of the optical fibers $3_1$ or $3_2$ and allocating the other diaphragm means to the free end of a light waveguide $5_1$ or $5_2$ belonging to the other transirradiation direction.

Figure 2:
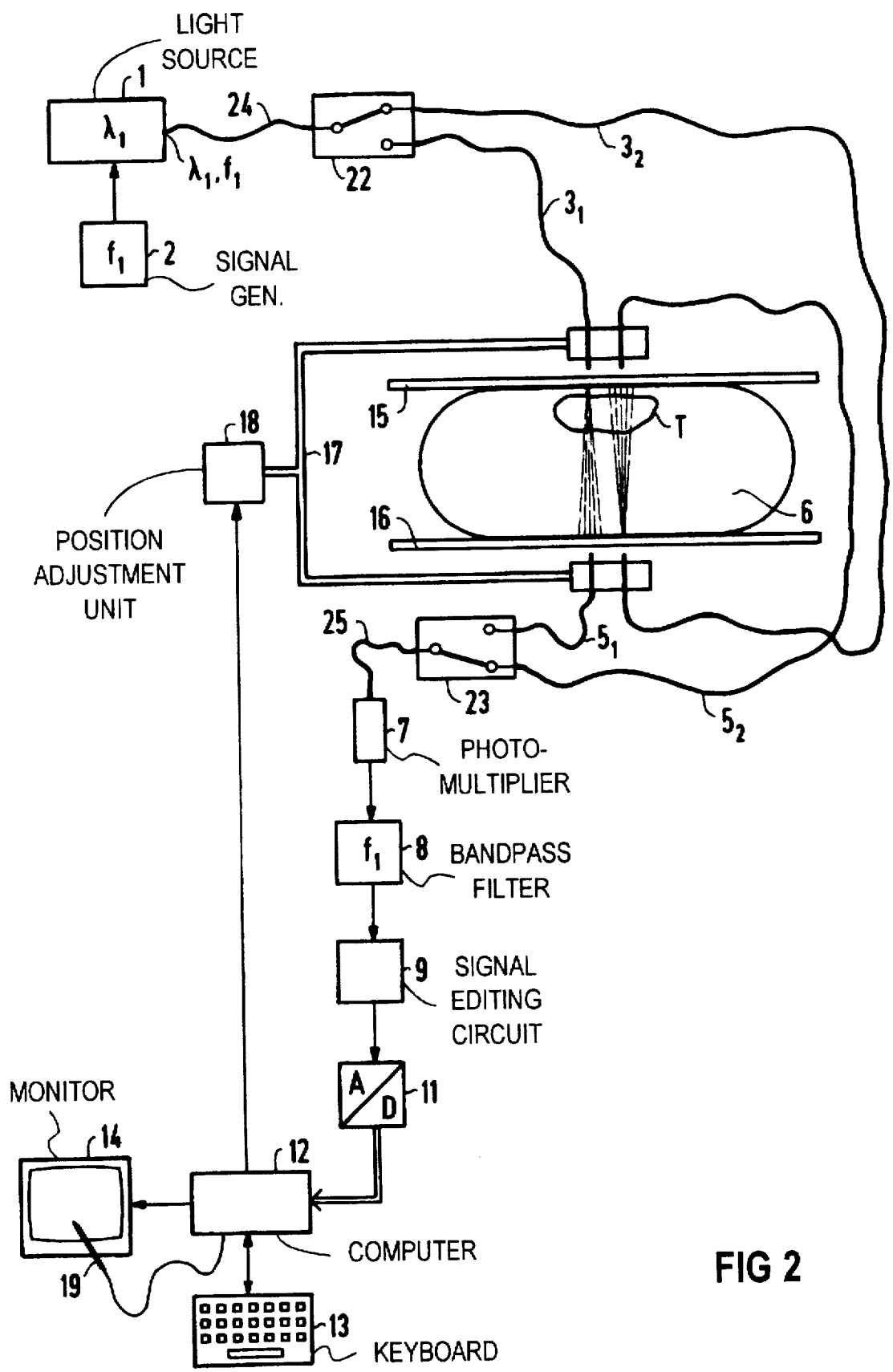

The apparatus according to FIG. 2 initially differs from that set forth above in that only one light source 1 with signal generator 2 is provided, this generating light of the wavelength $\lambda_1$ amplitude-modulated with the frequency $f_1$, in that only one photomultiplier 7, one band-pass filter 8 with the center frequency $f_1$, and one signal editing circuit 9 are present and in that the multiplexer 10 is absent since it is not needed.

In order nonetheless to be able to bidirectionally transirradiate the subject 6, two switchover units 22 and 23 are provided; these can be optomechanical or electrooptical switches. The switchover unit 22, to which the light source 1 is connected via a preferably fiber-optic light waveguide 24, serves the purpose of selectively coupling the light of the light source 1 into the light waveguide $3_1$ or into the light waveguide $3_2$ and thus of beaming permitting emission into the subject 6 proceeding from the one or the other side. The switchover unit 23, which is connected to the photomultiplier via a preferably fiber-optic light waveguide 25, serves the purpose of selectively connecting the photomultiplier 7 to the light waveguide $5_1$ or to the light waveguide $5_2$. The switchover units 22 and 23 are actuated in alternation by the electronic computational unit 12 such that either the light of the light source 1 is emitted into the subject 6 via the light guide fiber $3_1$ and the parts of the light transmitted through the subject 6 and received with the light waveguide $5_1$ are supplied to the photomultiplier 7, or the light of the light source 1 is supplied to the subject 6 via the light waveguide $3_2$ and the parts transmitted through the subject 6 and received with the light waveguide $5_2$ are supplied to the photomultiplier 7. The switching ensues, for example, with a frequency of 200 Hz. Thus the subject 6 is quasi-simultaneously bidirectionally transirradiated.

The apparatus according to FIG. 2 offers the advantage of reduced outlay since the outlay for the two switchovers 22 and 23 is less than the savings achieved by the use of only one light source 1, one photomultiplier 7, one band-pass filter 8, one signal editing circuit 9 and no multiplexer.

Figure 3:
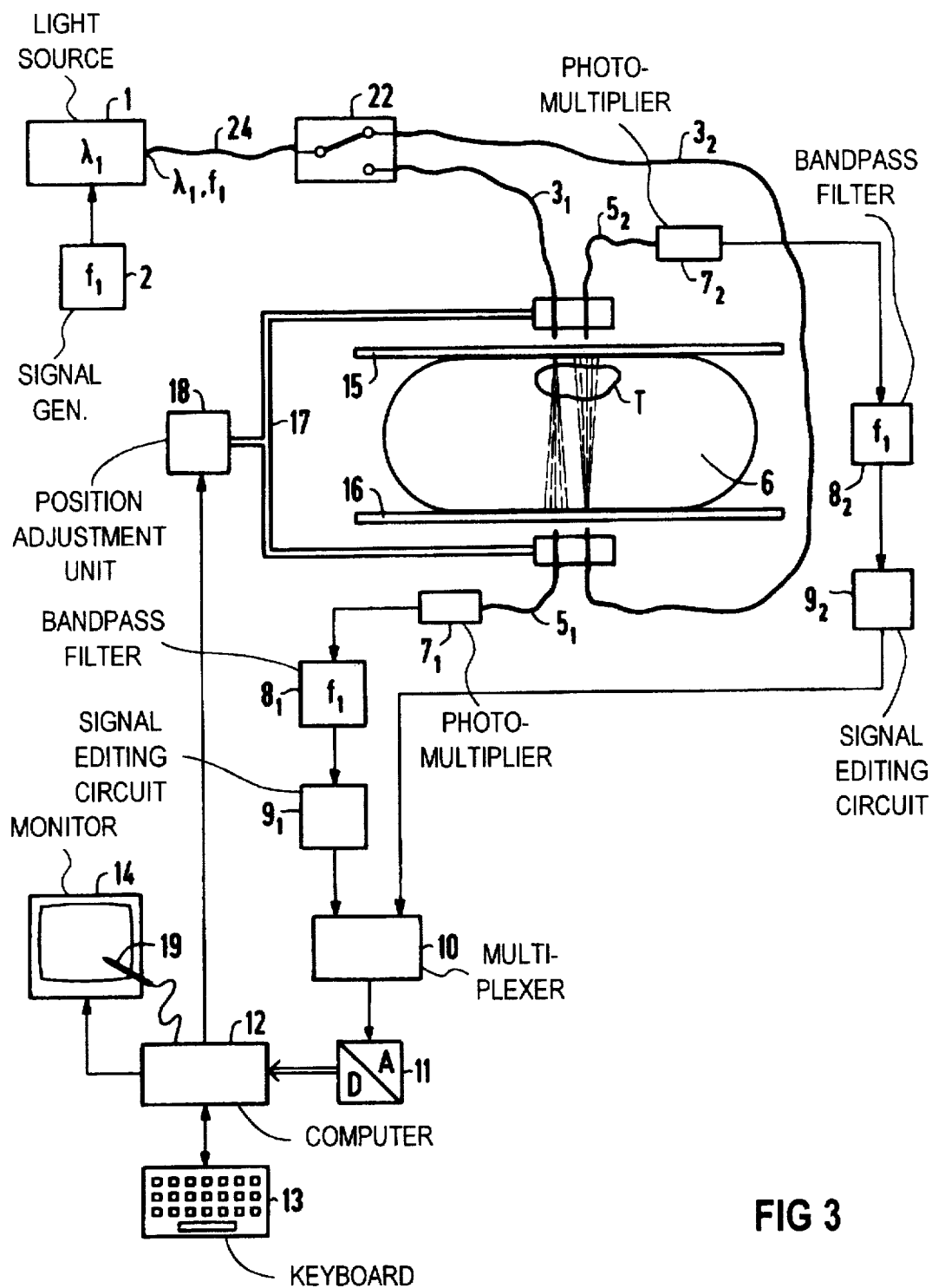

As is shown as an of example with reference to the embodiment of FIG. 3, there is also the possibility of mixed forms between the embodiments according to FIGS. 1 and 2. Thus, the embodiment of FIG. 3 is constructed analogously to FIG. 2 at the "transmitter side", i.e. only one light source 1 is present whose light can be selectively coupled by the switchover unit 22 into the light waveguide $3_1$ or into the light waveguide $3_2$. At the "reception side", the embodiment of FIG. 3 is constructed analogously to that according to FIG. 1, i.e. two photomultipliers $7_1$ and $7_2$, two band-pass filters $8_1$ and $8_2$, two signal editing circuits $9_1$ and $9_2$ and a 2:1 analog multiplexer 10 are provided. Since only one light source $1_1$ whose light is amplitude-modulated with the frequency $f_1$ is employed, both band-pass filters $8_1$ and $8_2$ have the center frequency $f_1$.

An apparatus can also be realized that is fashioned according to FIG. 1 at the "transmitter side" and according to FIG. 2 at the "receiver side".

Figure 4:
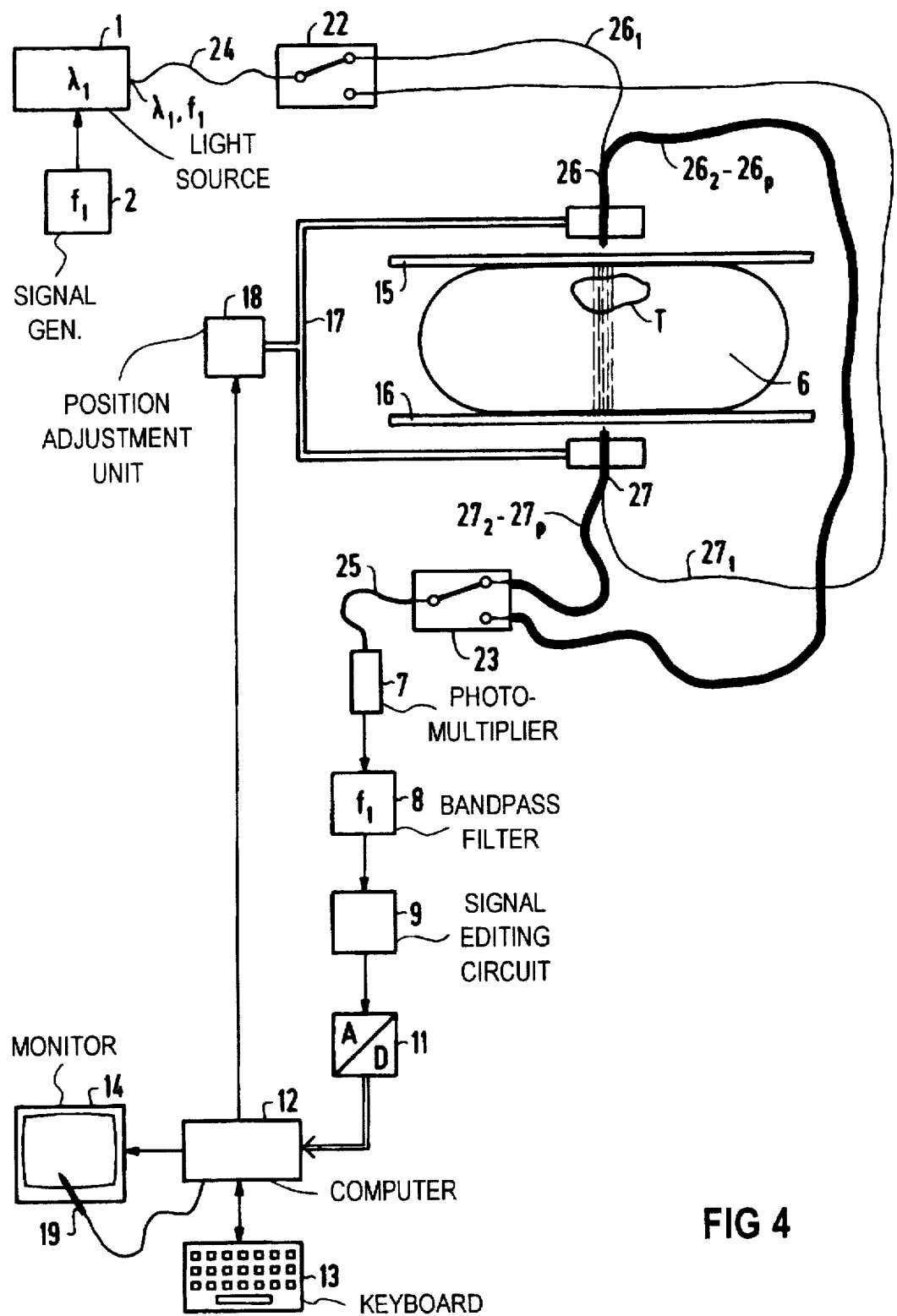

The embodiment according to FIG. 4 differs from that according to FIG. 2 in that two light guide fiber bundles 26 and 27 are provided instead of the light waveguides $3_1$ and $3_2$ and $5_1$ and $5_2$, each of these being composed of a plurality p of light guide fibers.

The central light guide fiber $26_1$ of the light guide fiber bundle 26 and the central light guide fiber $27_1$ of the light guide fiber bundle 27 are connected to the switchover unit 22 and correspond in function to the light waveguides $3_1$ and $3_2$ of the exemplary embodiment according to FIG. 2. The remaining light guide fibers $26_2$ through $26_p$, or $27_2$ through $27_p$, of the light guide fiber bundles 26 and 27 are connected to the switchover unit 23 and correspond in function to the light waveguides $5_1$ and $5_2$ of the exemplary embodiment according to FIG. 2. The free end of the light guide fiber bundle 26, moreover, is shown magnified in FIG. 5, showing twenty one light guide fibers $26_1$ through $26_{21}$ (p=21), only a few thereof being provided with reference characters in FIG. 5 and the central light guide fiber $26_1$ being shown shaded.

Dependent on the transirradiation direction, the free ends of the light guide fiber bundles 26 and 27 function as a light exit zone or as a light entry zone. The free ends of the light guide fiber bundles 26 and 27 are accepted in the carrier such that, given absence of a subject 6, the light emerging from the central light guide fiber $26_1$ or $27_1$ enters into the respective other central light guide fiber $27_1$ or $26_1$. By contrast to the above-described exemplary embodiments, wherein slight deviations of the tissue traversed by the light in both transirradiation directions are present, an exactly bidirectional transirradiation is thereby possible.

An improved signal-to-noise ratio is achieved as a result of the fact that a plurality of light guide fibers $26_2$ through $26_p$ or $27_2$ through $27_p$ serve the purpose of accepting parts of the transmitted light emerging from the subject 6. As a consequence of scatter phenomena, the transmitted light does not emerge at one location lying opposite the irradiation points and corresponding in size thereto, but instead emerges from the subject 6 in a larger area surrounding the latter location.

Figure 5:
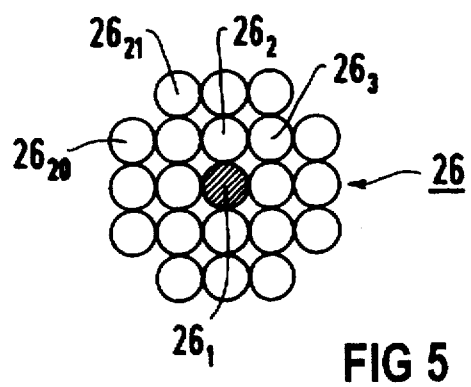
FIG. 5 shows a detail of the apparatus of FIG. 4.
Figure 6:
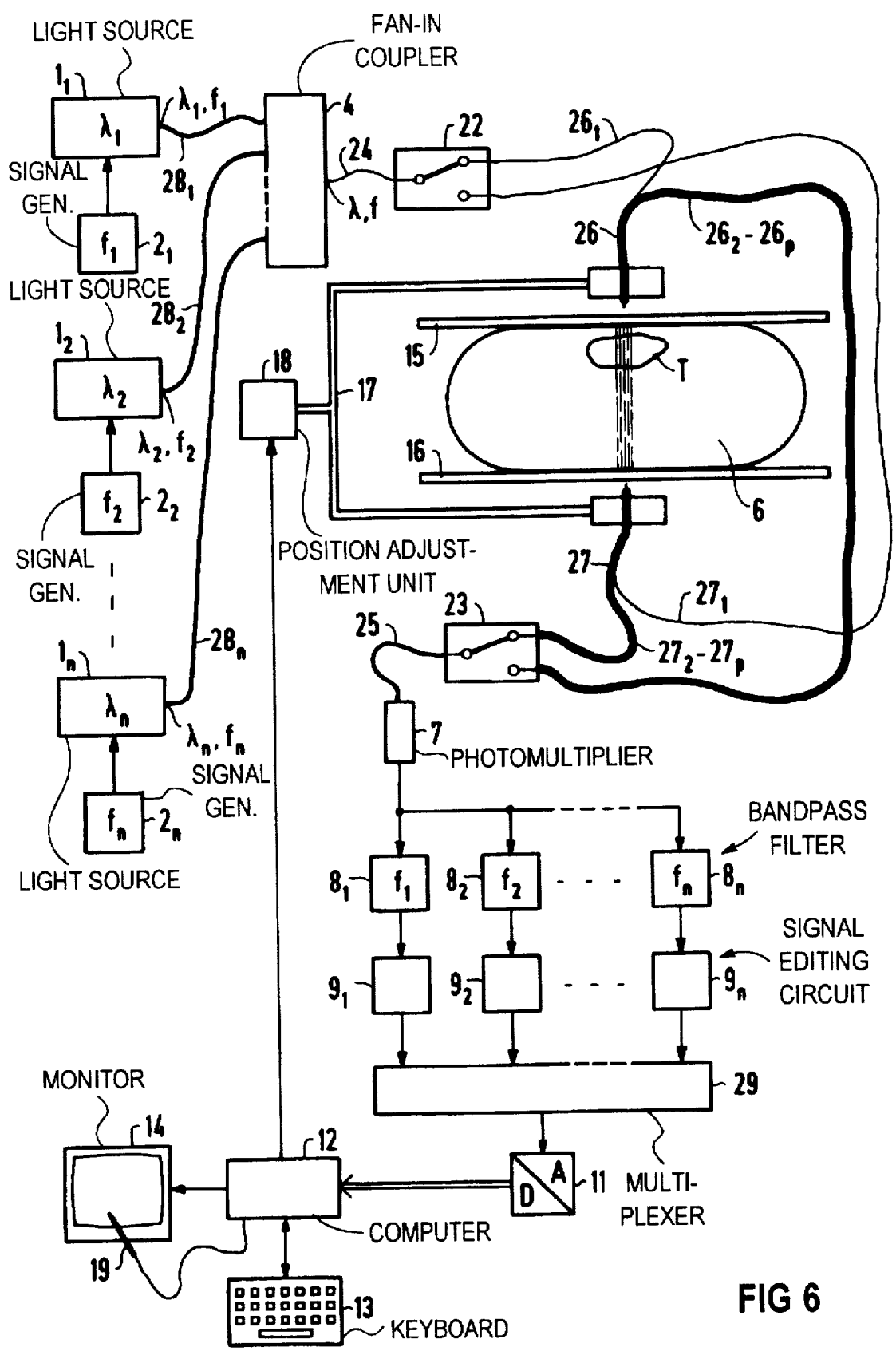
FIG. 6 is a schematic blocked diagram of a modified version of the apparatus according to FIGS. 4 and 5.

The embodiment according to FIG. 6 differs further from that according to FIGS. 4 and 5 in that spectroscopic examinations are also possible. To this end, a plurality of light sources $1_1$ through $1_n$ is provided, these respectively generating light of different wavelengths $\lambda_1$ through $\lambda_n$ that is amplitude-modulated with different frequencies $f_1$ through $f_n$ with the assistance of respective signal generators $2_1$ through $2_n$. The light of the light sources $1_1$ through $1_n$ is supplied via fiber-optic light waveguides $28_1$ through $28_n$ to a light waveguide fan-in coupler 4 that has n inputs respectively connected to the light waveguides $28_1$ through $28_n$ and an output to which the light waveguide 24 is connected.

In the case of the exemplary embodiment according to FIG. 6, thus, light that arises from the superimposition of the light respectively emitted by the light sources $1_1$ through $1_n$ with the light waveguide fan-in coupler 4 is emitted into the subject 6. The subject 6 is thus simultaneously supplied with light of the different wavelengths $\lambda_1$ through $\lambda_n$ for the respective transirradiation direction at a location that is respectively the same for all wavelengths $\lambda_1$ through $\lambda_n$.

Demodulator means in the form of band-pass filters $8_1$ through $8_n$ are provided in order to be able to acquire signals with respect to the intensity of the light of the different wavelengths $\lambda_1$ through $\lambda_n$ from the signal of the photomultiplier 7 corresponding to the received part of the light transmitted through the subject 6, whose curve over time represents the curve over time of the intensity of the received light insofar as it corresponds to the amplitude envelope of the received light. The center frequencies $f_1$ through $f_n$ thereof correspond as exactly as possible to the modulation frequencies $f_1$ through $f_n$. Electrical signals that represent the intensity of the light components arising from the light sources $1_1$ through $1_n$ in the received light supplied to the subject 6 and transmitted therethrough are thus respectively available at the outputs of the band-pass filters $8_1$ through $8_n$. These electrical signals respectively proceed to signal editing circuits $9_1$ through $9_n$ wherein signal editing adapted to the particular examination case ensues. The output signals of the signal editing circuits $9_1$ through $9_n$ are supplied to an n:1 multiplexer 29 whose output is connected to the analog/digital converter 11.

Per scan position, thus, the electronic computational unit 12 has instead of one data pair corresponding to both transirradiation directions, but a plurality of data pairs available to it, corresponding to the plurality n of different wavelengths, each representing the two transirradiation directions for a different wavelength. One can proceed in the above-described way with the images produced on the basis of the data by the electronic computational unit 12 and displayed on the monitor 14 as needed. The combining of image information arising from different images to form a new, higher-contrast image is thus not limited to the images of one image pair belonging to one of the wavelengths $\lambda_1$ through $\lambda_n$. On the contrary, there is also the possibility of combining image information from images belonging to different wavelengths $\lambda_1$ through $\lambda_n$ to form a new, higher-contrast image.

Whereas the amplitude modulation of the employed light in the case of the exemplary embodiments according to FIGS. 1 and 6 also serves the purpose of being able to recognize the transirradiation direction or the respective wavelength $\lambda_1$ through $\lambda_n$, the amplitude modulation of the light is provided in the other exemplary embodiments only to suppress influences of ambient light.

In the exemplary embodiments according to FIGS. 1 through 3, the computational unit 12 can compensate for the offset of the two transirradiation directions. This is easily possible by a coordinate transformation, particularly when the offset—in terms of magnitude and direction—corresponds to the spacing between two neighboring scan positions or to a whole multiple thereof.

The amplitude modulation described in conjunction with the exemplary embodiments is not the only usable modulation method; however, modulation and demodulation become especially simple in the case of amplitude modulation.

In the described exemplary embodiments, the light emerging from the subject 6 is respectively supplied to the photomultiplier 7 or to the photomultipliers $7_1$ and $7_2$ via light waveguides. There is also the possibility—in a way that is not shown—of arranging the photomultiplier 7, or the photomultipliers $7_1$ and $7_2$, such that the light emerging from the subject 6 can be directly picked up. In this case, the photomultiplier 7, or the photomultipliers $7_1$ and $7_2$, would have to be attached to the carrier 17 of the scan means in a suitable way. Instead of a photomultiplier, the means for detection can alternative be a photodiode or a CCD.

An LED, LCD or plasma display can be provided as the display means instead of the monitor 14.

The means described in conjunction with the exemplary embodiments for emitting light into the subject, which include one or more light sources, one or more signal generators, various light waveguides, possibly the switchover units 22 and 23 as well as, possibly, the light waveguide fan-in coupler 4, can also be differently fashioned. Thus, for example, the irradiation with the light can alternatively so be accomplished with a mirror arrangement.

The fashioning of the scan means is also to be understood as only an example. Some other structure of the scan means as well as scan motions deviating from the described scan motion are possible.

In order to avoid overexposure of the photomultiplier or photomultipliers due to a direct irradiation with the light to be emitted into the subject, there is the possibility of controlling the scan motion such as with the assistance of a suitable sensor means so that only those scan positions among the possible scan positions at which it is assured that the subject 6 is located between the light exit and the light entry zones are permitted.

Although modifications and changes may be suggested by those skilled in the art, it is the intention of the inventor to embody within the patent warranted hereon all changes and modifications as reasonably and properly come within the scope of his contribution to the art.

I claim as my invention:

1. An apparatus for examining tissue with light, comprising:
   means for bidirectionally transirradiating tissue with light from different transirradiation directions;
   means for detecting light passing through said tissue in each transirradiation direction upon said light emerging from said tissue,
   said means for detecting comprising a single detector, and first and second detector light guide means having respective light entry faces disposed for receiving said light emerging from said tissue in said two directions, and means for alternatingly supplying said light from said respective entry faces to said single detector.

2. An apparatus as claimed in claim 1, wherein said first and second detector light guide means comprise fiber-optic detector light guide means.

3. An apparatus as claimed in claim 1, wherein said first and second light guide means comprise fiber-optic light guide means and wherein said first and second detector light guide means comprise fiber-optic light guide means, each fiber-optic light guide means containing an optical fiber bundle having at least one light guide fiber which conducts light in a first of said transirradiation directions and at least one other light guide fiber which conducts light in a second of said transirradiation directions.

4. An apparatus for examining tissue with light, comprising:
   means for bidirectionally transirradiating tissue with light;
   scan means for moving said means for bidirectionally transirradiating said tissue with light relative to said tissue at a plurality of different scan positions; and
   means for detecting light passing through said tissue in each transirradiation direction upon said light emerging from said tissue.

5. An apparatus as claimed in claim 4, wherein said means for bidirectionally transirradiating tissue comprise means for quasi-simultaneously bidirectionally transirradiating tissue with light.

6. An apparatus as claimed in claim 4, wherein said means for bidirectionally transirradiating tissue with light comprise means for simultaneously irradiating tissue in two transirradiation directions.

7. An apparatus as claimed in claim 6, further comprising means for differently modulating the light respectively transmitted in said two transirradiation directions using a first modulation in a first of said two directions and a second modulation in a second of said two directions.

8. An apparatus as claimed in claim 7, wherein said means for differently modulating comprise means for amplitude-modulating the light in said first direction with a modulation frequency and for modulating the light in said second direction with a second modulation frequency.

9. An apparatus as claimed in claim 4, further comprising diaphragm means for alternatingly blocking light from said respective transirradiation directions from reaching said means for detecting.

10. An apparatus as claimed in claim 4, wherein said means for bidirectionally transirradiating tissue with light comprise a first light source and a second light source, wherein said means for detecting comprise a first detector and a second detector, and wherein light in a first of said transirradiation directions emanates from said first light source and is detected by said first detector and light in a second of said transirradiation directions emanates from said second light source and is detected by said second detector.

11. An apparatus as claimed in claim 10 comprising means for simultaneously activating said first light source and said first detector and said second light source and said second detector.

12. An apparatus as claimed in claim 10 further comprising means for simultaneously activating only said first light source and said first detector and subsequently simultaneously activating only said second light source and said second detector.

13. An apparatus as claimed in claim 4, wherein said means for bidirectionally transirradiating tissue comprise a single light source connected to first and second light guides, said light guides having respective light exit faces from which light from said single light source respectively emerges in one of two transirradiation directions.

14. An apparatus as claimed in claim 13, wherein said first and second light guide means comprise fiber-optic light guide means.

15. An apparatus for examining tissue with light, comprising:
   means for bidirectionally transirradiating tissue with light from different transirradiation directions;
   means for detecting light passing through said tissue in each transirradiation direction upon said light emerging from said tissue and for emitting detector output signals; and evaluation means, supplied with said detector output signals for analyzing said detector output signals.

16. An apparatus as claimed in claim 15, wherein said bidirectional transirradiation directions have respective optical axes which are offset relative to each other, and wherein said evaluation means comprises means for eliminating said offset.

17. An apparatus as claimed in claim 16 further comprising scan means for moving said means for bidirectionally transirradiating said tissue with light relative to said tissue for bidirectionally transirradiating said tissue with light from a plurality of different scan positions and wherein said means for bidirectionally transirradiating said tissue comprise means for bidirectionally transirradiating said tissue along respective optical axes having an offset which is equal in magnitude and direction for two neighboring scan positions.

18. An apparatus as claimed in claim 16 further comprising scan means for moving said means for bidirectionally transirradiating said tissue with light relative to said tissue for bidirectionally transirradiating said tissue with light from a plurality of different scan positions and wherein said means for bidirectionally transirradiating said tissue comprise means for bidirectionally transirradiating said tissue along respective optical axes having an offset in a scan position which is a whole multiple in terms of magnitude and direction to an offset in a neighboring scan position.

19. An apparatus for examining tissue with light, comprising:

means for bidirectionally transirradiating tissue from different transirradiation directions simultaneously with light, the light from said different directions being of respectively different wavelengths;

means for detecting light passing through said tissue in each transirradiation direction upon said light emerging from said tissue and for emitting a respective detector output signal for light of each of said wavelengths; and signal processing means, supplied with said detector output signals, for identifying light of each of said different wavelengths in the light detected by said means for detecting.

* * * * *